United States Patent [19]
Kassatly

[11] Patent Number: 5,578,077
[45] Date of Patent: Nov. 26, 1996

[54] MECHANICAL HEART, BODY FLUID AND DRUG INFUSION PUMP

[76] Inventor: Samuel A. Kassatly, 4150 Middlefield Rd., Palo Alto, Calif. 94303

[21] Appl. No.: 292,877

[22] Filed: Aug. 19, 1994

Related U.S. Application Data

[63] Continuation-in-part of Ser. No. 144,745, Oct. 28, 1993, which is a continuation-in-part of Ser. No. 17,030, Feb. 12, 1993, which is a continuation-in-part of Ser. No. 826,372, Jan. 27, 1992, which is a continuation-in-part of Ser. No. 573,539, Aug. 27, 1990, Pat. No. 5,157,491, which is a continuation-in-part of Ser. No. 457,403, Dec. 18, 1989, Pat. No. 4,975,771, which is a continuation-in-part of Ser. No. 308,826, Feb. 10, 1989, Pat. No. 4,903,126, which is a continuation-in-part of Ser. No. 258,722, Oct. 17, 1988, abandoned.

[51] Int. Cl.$^6$ ............................... A61M 1/10; A61K 9/22
[52] U.S. Cl. .............................. 623/3; 623/11; 604/892.1; 415/900; 424/422
[58] Field of Search ...................................... 623/3, 11–12, 623/66; 604/890.1, 891.1, 892.1; 424/422–424; 415/900; 600/29–30

[56] References Cited

U.S. PATENT DOCUMENTS

| | | |
|---|---|---|
| 4,547,137 | 10/1985 | Terauchi et al. .......................... 418/55 |
| 4,588,404 | 5/1986 | Lapeyre ...................................... 623/3 |

*Primary Examiner*—Randall L. Green
*Assistant Examiner*—P. Zuttarelli
*Attorney, Agent, or Firm*—Samuel A. Kassatly

[57] ABSTRACT

The present invention describes a new pump which can be used as a mechanical heart, as a body fluid, as a drug infusion pump, and in similar or related applications for the circulation of body fluids including but not limited to blood and oxygenated air. The pump includes a scroll type pump that has been modified for medical applications. The pump includes two scroll involute spiral elements that are maintained at an angular and radial offset so that both spiral elements interfit to make a plurality of line contacts between their spiral curved surfaces to thereby seal off and define at least one pair of fluid pockets. The relative orbital motion of the two spiral elements shifts the line contact along the spiral curved surfaces thus causing the fluid pockets to change in volume. Since the volume of the fluid pockets increases or decreases, depending on the direction of the orbital motion, the scroll type pump is capable of either compressing, expanding or pumping the body fluids.

20 Claims, 7 Drawing Sheets

MECHANICAL HEART, BODY FLUID AND DRUG INFUSION PUMP

RELATED APPLICATIONS

This is a continuation in part of application Ser. No. 08/144,745 filed on Oct. 28, 1993, now pending; which is a continuation in part of application Ser. No. 08/017,030 filed Feb. 12, 1993, now pending; which is a continuation in part of application Ser. No. 07/826,372 filed on Jan. 27, 1992, now pending; which is a continuation in part of application Ser. No. 07/573,539 filed Aug. 27, 1990, now U.S. Pat. No. 5,157,491; which is a continuation in part of application Ser. No. 07/457,403 filed Dec. 18, 1989, now U.S. Pat. No. 4,975,771; which is a continuation in part of application Ser. No. 07/308,826 filed Feb. 10, 1989, now U.S. Pat. No. 4,903,126; which is a continuation in part of Ser. No. 7/258,722 filed Oct. 17, 1988, now abandoned.

BACKGROUND OF THE INVENTION

1. Technical Field

The present invention relates in general to the medical field, and it more particularly relates to a new pump which can be used as a mechanical heart, as a body fluid, as a drug infusion pump, and in similar or related applications for the circulation of body fluids including but not limited to blood and oxygenated air.

2. Background Information

Several attempts have been made to implement a replacement heart, however, none of these attempts have been completely satisfactory. Body fluid and drug infusion pumps on the other hand, have met with much better success. However, there is still an unsatisfied need for am improved pump which can be used as a mechanical heart, as a body fluid, as a drug infusion pump, and in similar or related applications for the circulation of body fluids including but not limited to blood and oxygenated air.

SUMMARY OF THE INVENTION

The present invention relates to a new pump which can be used as a mechanical heart, as a body fluid, as a drug infusion pump, and in similar or related applications for the circulation of body fluids including but not limited to blood and oxygenated air. The pump includes a scroll type pump that has been modified for medical applications.

The pump includes two scroll involute spiral elements that are maintained at an angular and radial offset so that both spiral elements interfit to make a plurality of line contacts between their spiral curved surfaces to thereby seal off and define at least one pair of fluid pockets. The relative orbital motion of the two spiral elements shifts the line contact along the spiral curved surfaces thus causing the fluid pockets to change in volume. Since the volume of the fluid pockets increases or decreases, depending on the direction of the orbital motion, the scroll type pump is capable of either compressing, expanding or pumping the body fluids.

BRIEF DESCRIPTION OF THE DRAWINGS

The above and other features of the present invention and the manner of attaining them, will become apparent, and the invention itself will be best understood, by reference to the following description and the accompanying drawings, wherein.

DESCRIPTION OF THE PREFERRED EMBODIMENT

Figure 1:
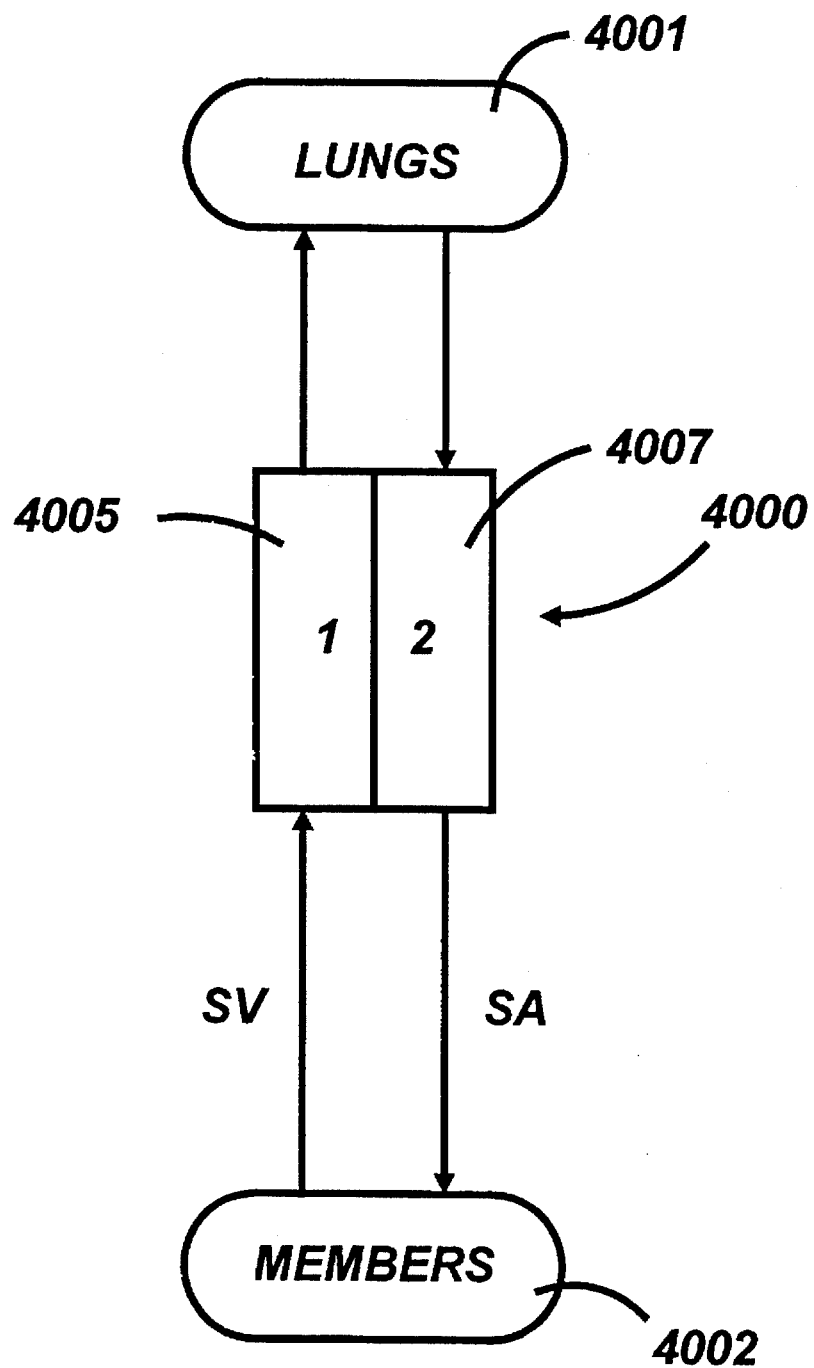
FIG. 1 is a very simplified block high level block diagram of a new artificial heart according to the present invention.

FIG. 1 is a very simplified block high level block diagram of a new artificial heart 4000 for replacing a natural heart. The artificial heart 4000 is shown as being interposed between the lungs 4001 and the rest of the body members 4002. In general, the artificial heart 4000, similarly to the natural heart, is divided into two chambers: a right chamber or pump 4005, and a left chamber or pump 4007. The right pump 4005 of the artificial heart 4000 is connected to the lungs 4001 via the pulmonary arteries and capillaries that are indicated by the arrow PA, and to the rest of the body members 4002 via the systemic veins and capillaries that are indicated by the arrow SV. The left pump 4007 of the artificial heart 4000 is connected to the lungs 4001 via the pulmonary veins and capillaries that are indicated by the arrow PV, and to the rest of the body members 4002 via the systemic arteries and capillaries that are indicated by the arrow SA.

Figure 2:
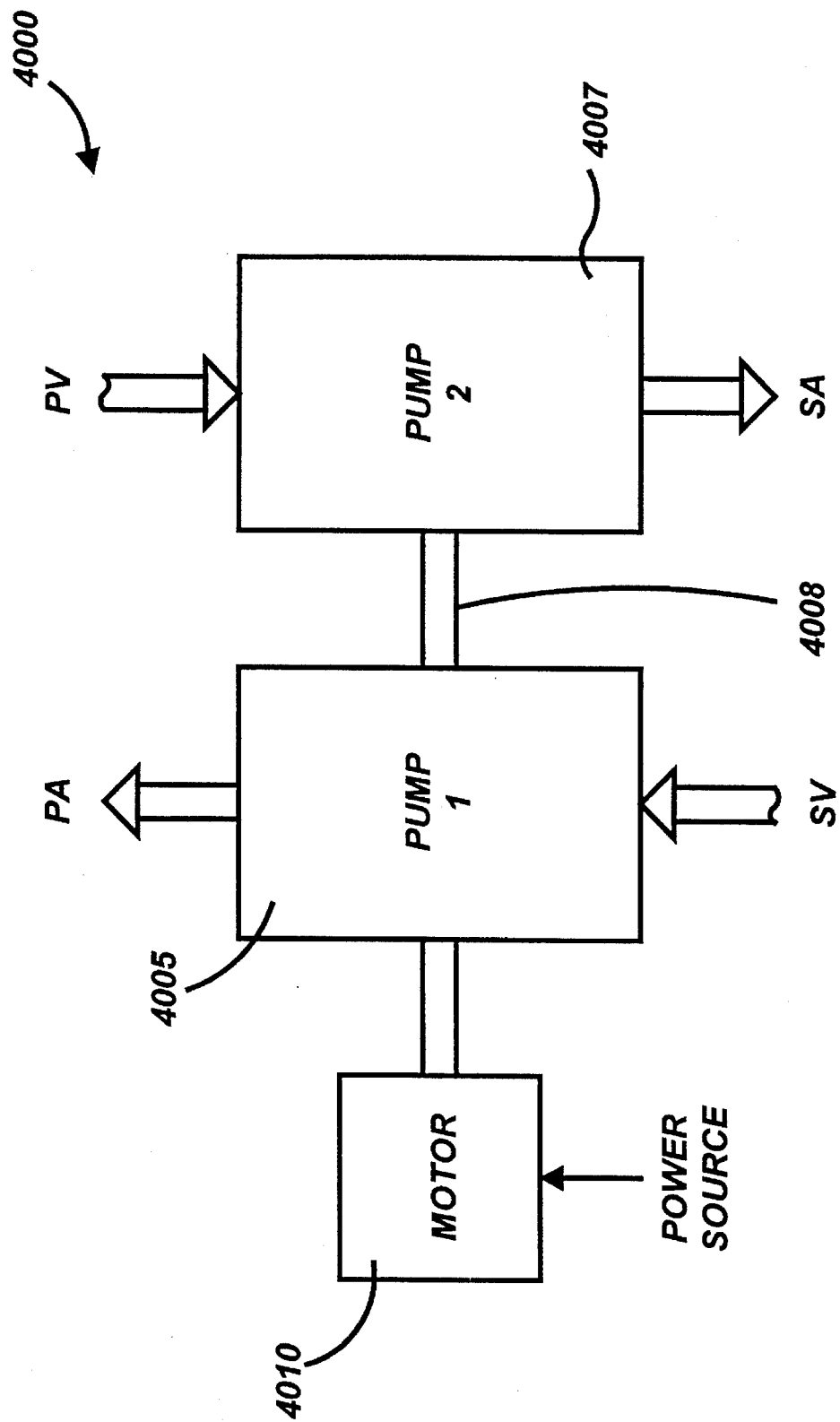
FIG. 2 is a more detailed, but still high level block diagram of the artificial heart of FIG. 55.

FIG. 2 is another more detailed, but still high level block diagram of the artificial heart 4000, illustrating the two pumps 4005 and 4007 as two blocks that are interconnected by a drive shaft 4008, which, in turn, is coupled to a motor 4010, for driving the pumps 4005 and 4007. It should be understood that while the pumps 4005 and 4007 are shown as being closely positioned, they can be physically separated and driven by different rotation means or by means of a flexible drive shaft 4008.

The pumps 4005 and 4007 are generally similar in design and construction. However, it is possible to design these pumps 4005 and 4007 differently so as to account for the physiological variances between the right and left chambers (auricles and ventricles) of the natural heart, without departing from the scope of the present invention. In operation, as the right pump 4005 pumps the venous blood toward the lungs 4001, the left pump 4007 pumps the arterial blood toward the body members 4002. Such pumping action can be simultaneous, delayed or programmable.

The artificial heart 4000 can be implantable or external. If implanted, the artificial heart 4000 is hermetically sealed in a fluid tight manner, and is further biocompatible. The housing 4008 for each pump 4005, or 4007 is relatively thin, and the ability to separate these two pumps 4005, 4007 provides an additional freedom of design, positioning, and adaptation to smaller cavities, such as in pediatric applications.

FIGS. 3 through 12 illustrate a sequence of cross sectional views of the pump 4005 in operation. The pump 4005 includes a scroll type pump that has been modified for medical applications. Scroll type compressors are well known and used in various fields, such as in the automotive industry, but none has yet been adapted for effective use in the medical field, and in particular as a heart replacement. One such conventional scroll type compressors is described in U.S. Pat. No. 4,547,137 to Terauchi, which is incorporated herein by reference.

The pump 4005 includes two scroll involute spiral elements 4011 and 4012 that are maintained at an angular and radial offset so that both spiral elements (or scroll members) 4011 and 4012 interfit to make a plurality of line contacts between their spiral curved surfaces to thereby seal off and define at least one pair of fluid pockets, such as the pockets P1 and P2. The relative orbital motion of the two spiral elements 4011 and 4012 shifts the line contact along the spiral curved surfaces and, therefore, the fluid pockets P1 and P2 change in volume. Since the volume of the fluid pockets increases or decreases, depending on the direction of the orbital motion, the scroll type pump 4005 is capable of either compressing, expanding or pumping fluids.

Figure 6:
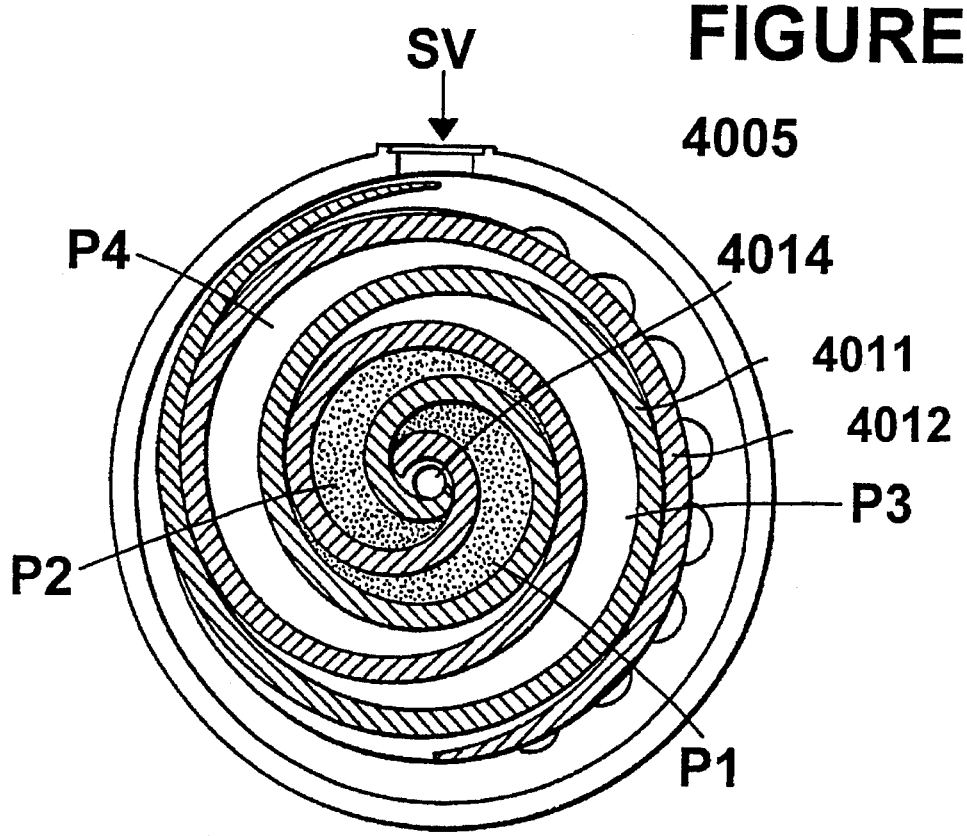
Figure 7:
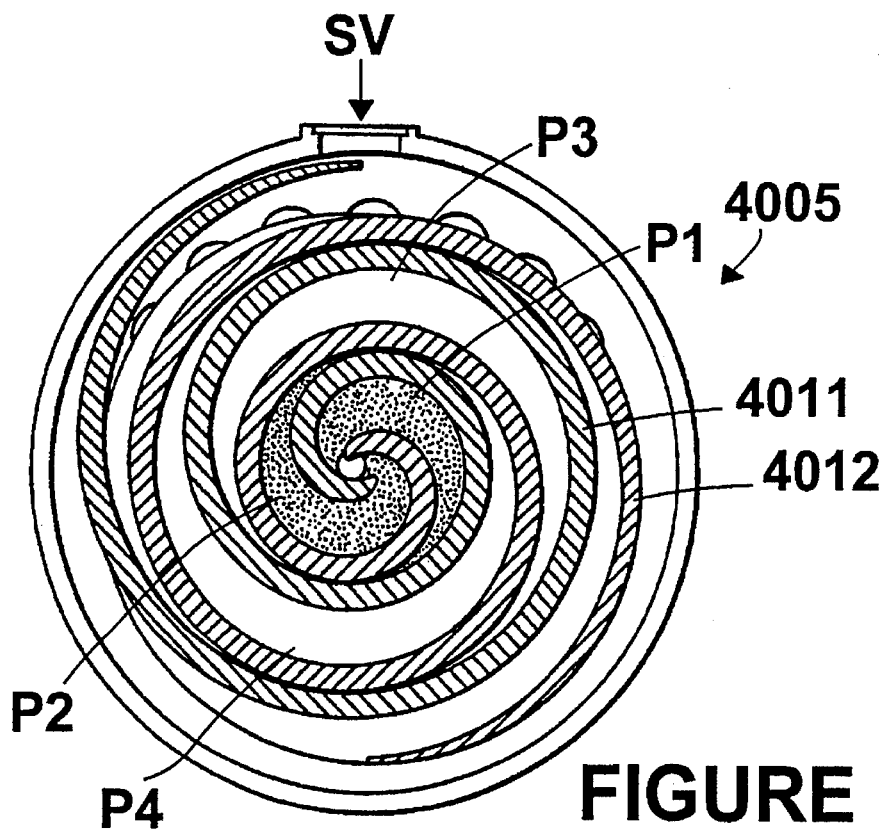
Figure 8:
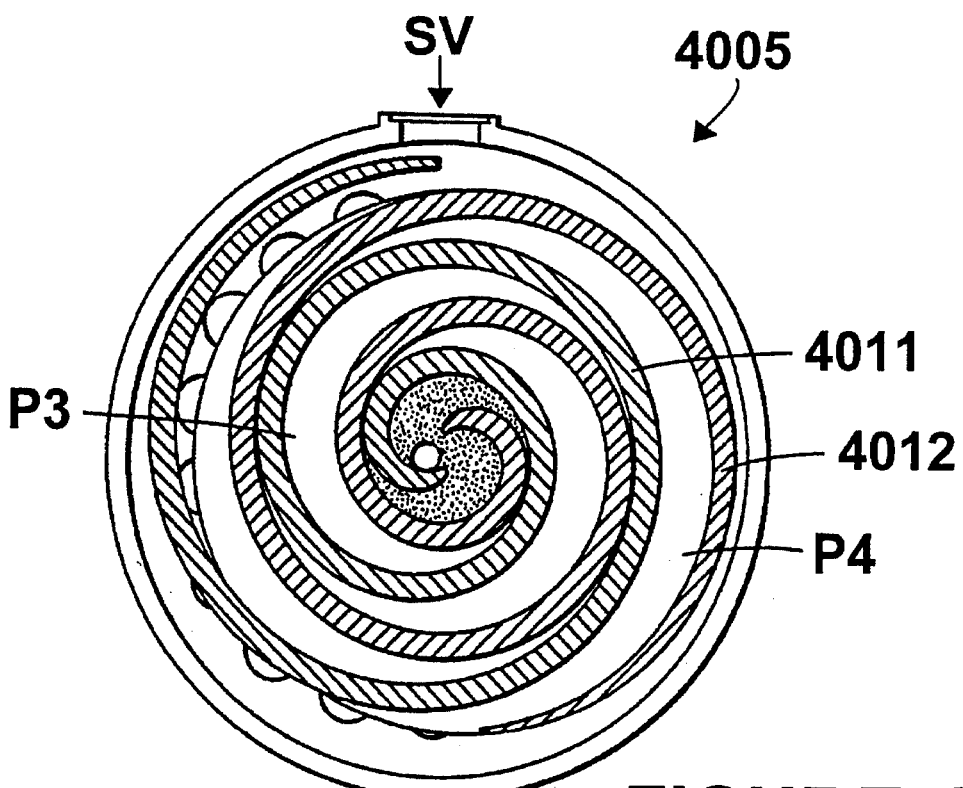
Figure 9:
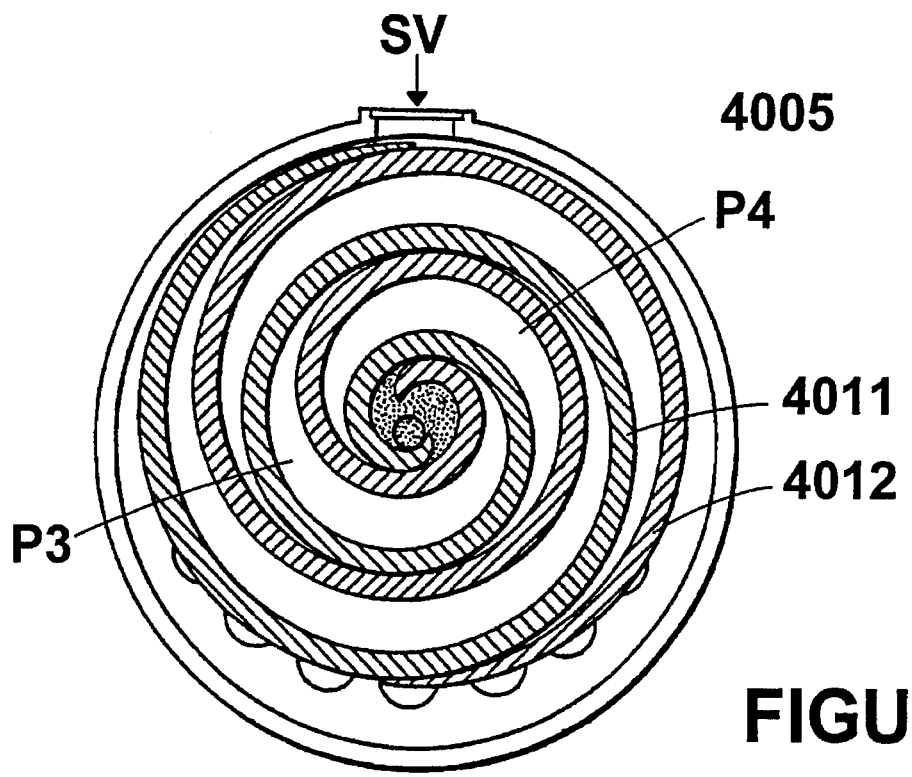
Figure 10:
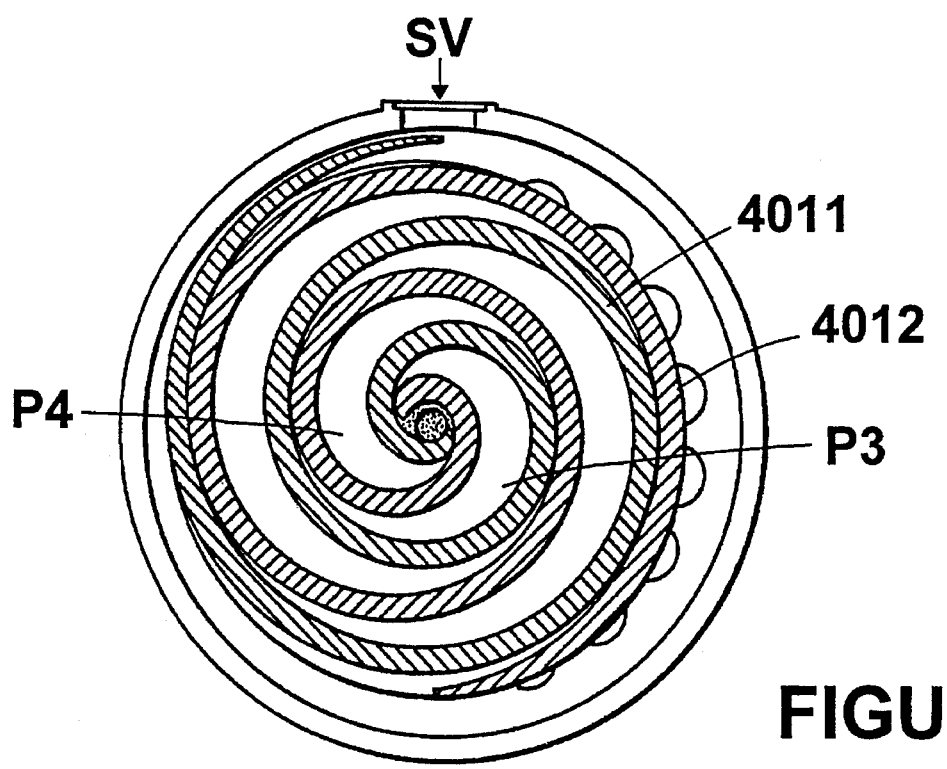
Figure 11:
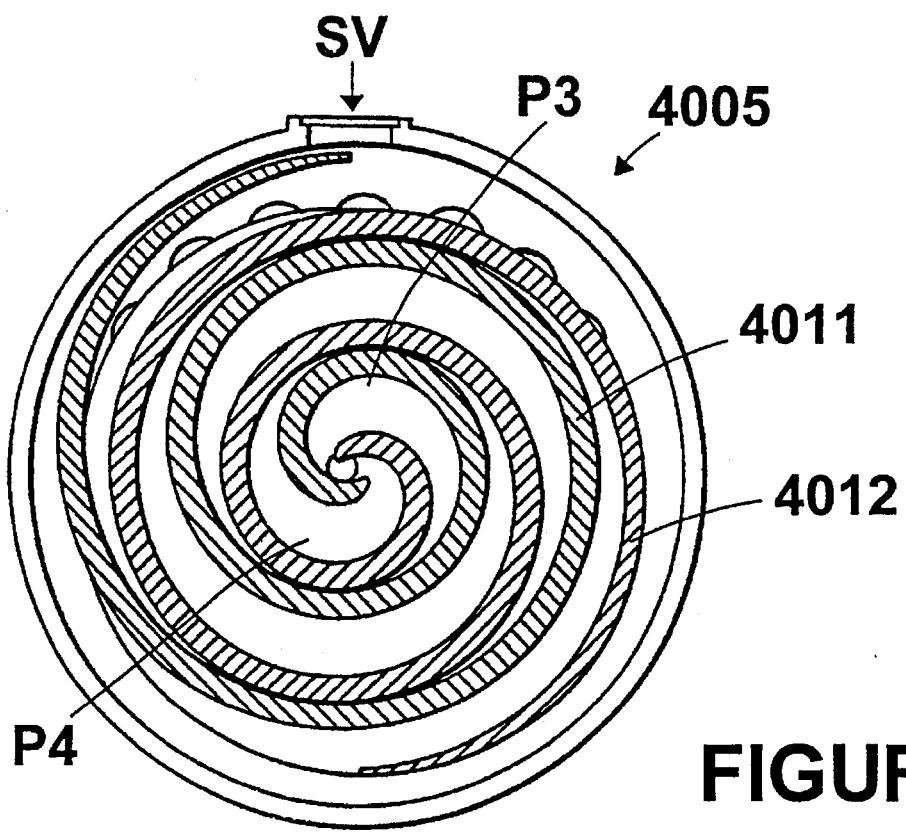
Figure 12:
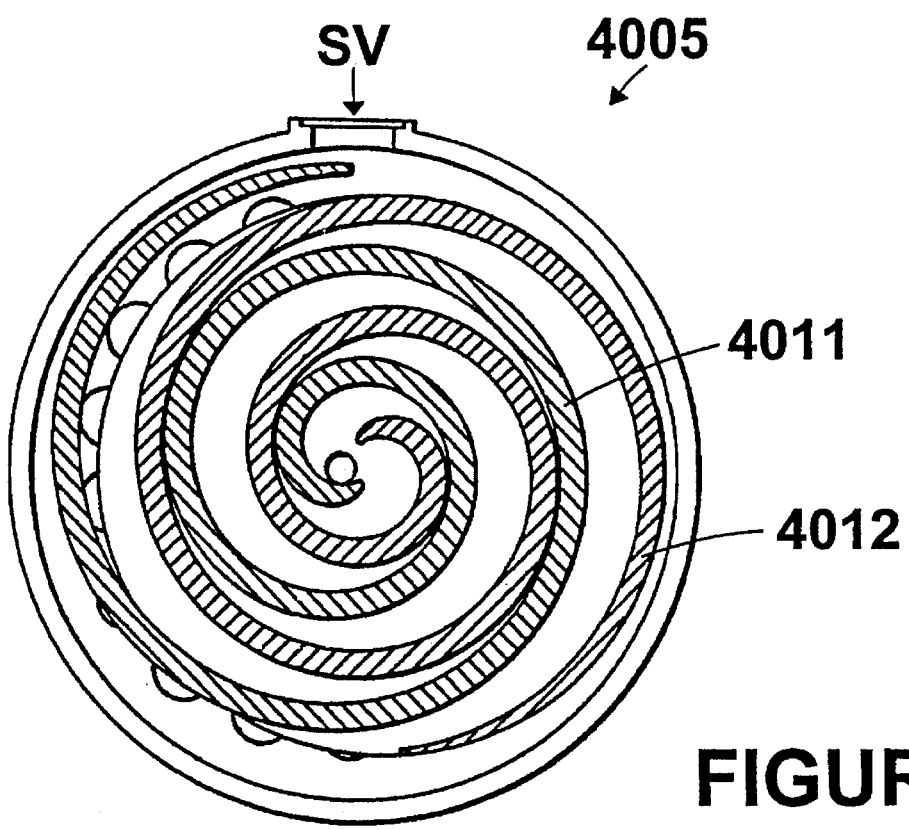

FIGS. 3 through 12 schematically illustrate the relative movement of the interfitting spiral elements 4011 and 4012 to compress the fluid. Throughout the states shown in FIGS. 3 through 12, the pair of fluid pockets P1 and P2 shift angularly toward the central narrow opening 4014 of the interfitting spiral elements 4011 and 4012, with the volume of each fluid pocket P1 and P2 being gradually reduced. Fluid pockets P1 and P2 are connected to each other in passing from the state shown in FIG. 5 to the state shown in FIG. 7, and as shown in FIG. 7, both fluid pockets merge at the central narrow opening 4014 and are completely connected to one another to form a single pocket. The volume of the connected single pocket is further reduced by a drive shaft revolution of about 90 degrees, as shown in FIGS. 8–10.

Figure 3:
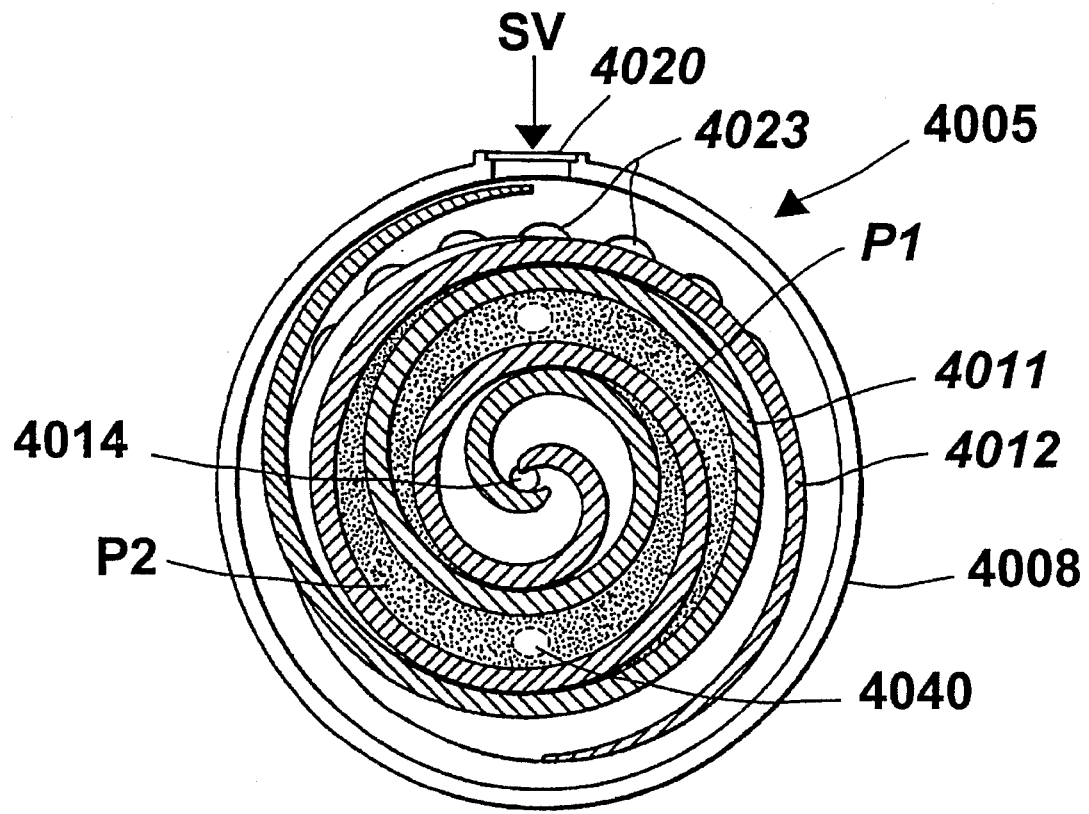
FIGS. 3 through 12 illustrate a sequence of cross sectional views of a pump (forming part of the artificial heart) in operation.

During the course of relative orbital movement, outer spaces which are open in the state shown in FIG. 3 change as shown in FIGS. 6 and 7 to form new sealed off fluid pockets P3 and P4 in which fluid is newly enclosed. The pump 4005 further includes an inlet opening 4020 for allowing the fluid to enter the pump 4005 via a valve, such as a reed valve (not shown), which will open at a predetermined inlet pressure. Alternatively, the valve can be programmed to allow a predetermined or controlled volume of fluid to enter the pump 4005. A plurality of suction ports 4023 are optionally provided to also allow the same or a different fluid to enter the pump 4005 to mix (sometimes gradually) under pressure with the first fluid passing through the inlet opening 4020 in the various fluid pockets, i.e., P1–P4, at different pressures, until the mixed fluid is dispensed, under pressure, through the central narrow outlet opening 4014. In certain applications it would be desirable to pulsate the fluid, and such pulsation can be controlled by the selective opening and closing of the inlet opening 4020 and the suction ports 4023.

In other applications, the fluid being pumped can be a liquid such as blood. The inlet valve is programmed or regulated so as to allow a specific amount of blood to enter the pump 4005. In some applications, it is possible to design the volume of the fluid pockets or chambers P3 and P4 (FIGS. 5–12) so as to contain a predetermined volume of blood. As these fluid pockets P3 and P4 move toward the outlet opening 4014, their respective volumes decrease, thus causing the blood contained therein to be "pumped". In a particular application, the volume of the blood admitted through the inlet port 4020 and captured by the fluid chambers P3 and P4 is about the same or somewhat larger than the volume of a central common chamber P, shown in FIG. 4. Different designs and applications would require different designs.

In another application, it would be desirable to introduce a combination of different fluids, such as a liquid and a gas, for instance blood and oxygen; or two liquids, for instance blood and drug to be dispensed either to the lungs 4001 (pump 4005) or to the body members 4002 (pump 4007). One fluid, such as blood is introduced via the inlet opening 4020 and the other fluid(s) is (are) introduced via the suction ports 4023. Thus, by introducing oxygen directly to the pump 4005 for mixing with the venous blood before it is pumped to the lungs 4001, the work required by the lungs 4001 to oxygenate the blood is reduced. This application is of particular interest to patients with fatigued or diseases lungs. As the fluids are introduced into the fluid pockets P3 and P4, via the inlet port 4020 and the suction ports 4023, they are mixed together. The gaseous fluid, being compressible, further aids in the pumping of the blood. The temperature, pressure and flow of the gaseous fluid can be selectively controlled. It is also conceivable to replace the lung or lungs with a pump similar to the pump 4005, whereby air or oxygen is introduced to, and compressed by the pump.

Figure 4:
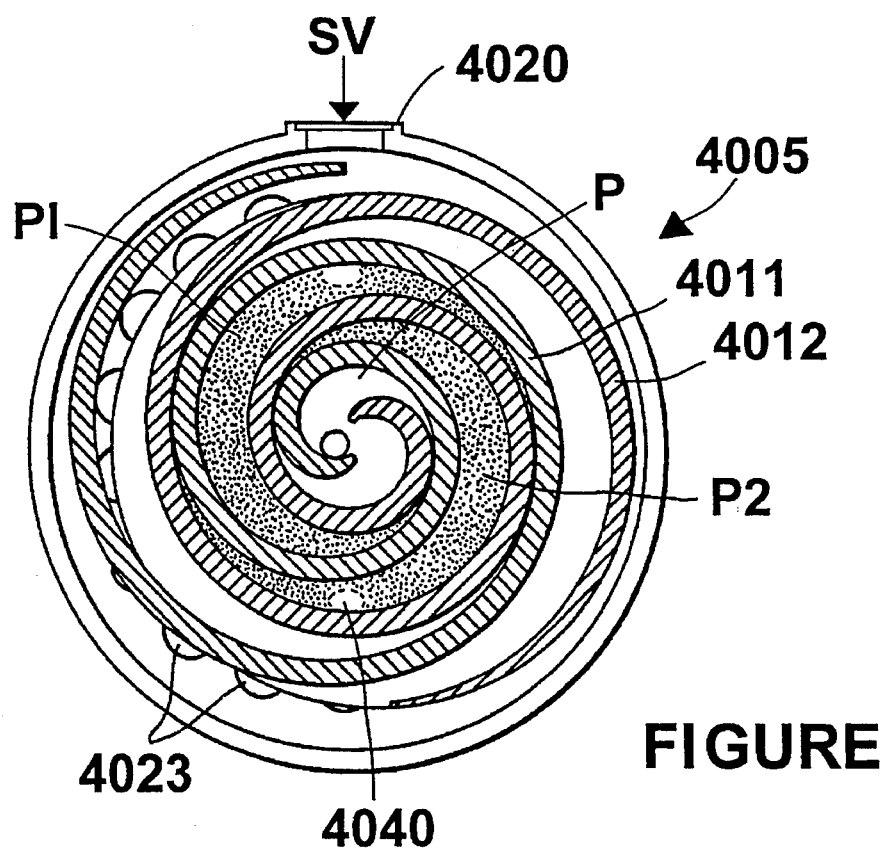
Figure 5:
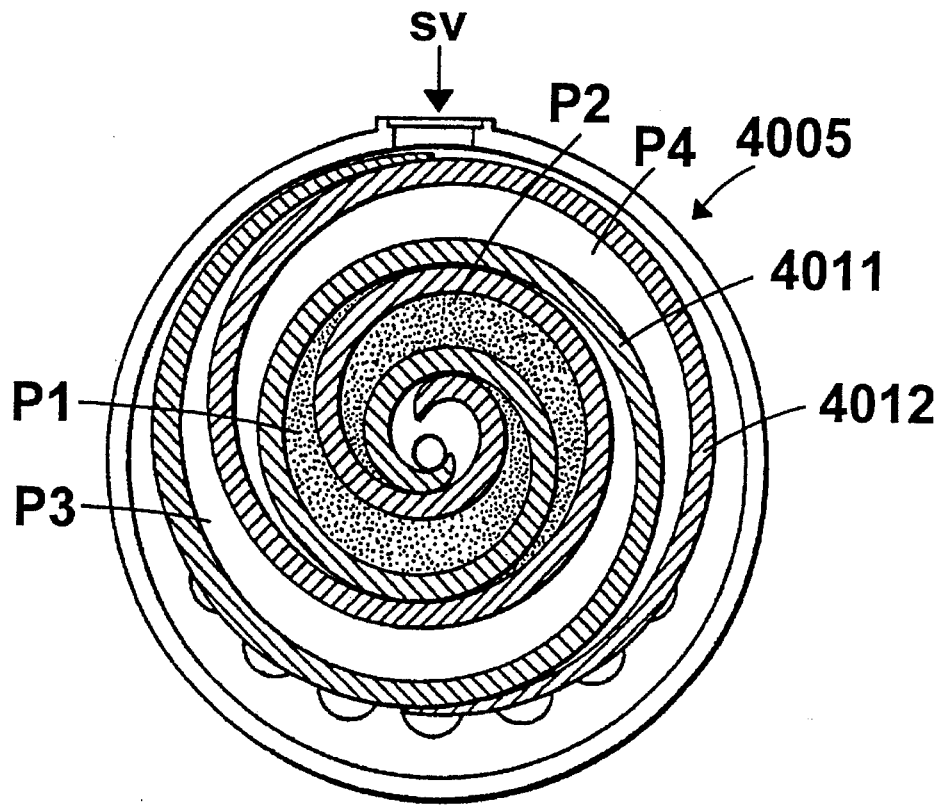

In another improvement, selected veins, i.e, the superior vena cava, are connected to the inlet port 4020, and other veins, i.e., the inferior vena cava, are connected to the suction ports 4023. Additionally, it is also possible to include a plurality of outlet ports 4040 (shown in dashed lines) with access to pre-selected fluid pocket positions, such as fluid pockets P1 and P2 (FIGS. 3 and 4). In this manner, it is possible to regulate the pressure along the moving fluid chambers. For instance, if pressure builds up above a preset level in the fluid chamber P1, a valve (not shown), such as a reed valve is opened (maybe temporarily) to allow fluid within the pocket to exit the pocket. The valve can be regulated so that the fluid is allowed to flow out of the pump 4005 either for a fixed period of time; to allow a specific volume of fluid to flow out; or to allow enough fluid to flow out until the pressure within the fluid chamber P1 is within an acceptable range. Alternatively, the valve can be opened permanently such that a preselected volume of blood, at a preselected pressure, is allowed to flow out of the pump 4005.

It should be understood that the spiral elements of the scroll type pumps can have various shapes, without departing from the scope of the invention. It should also be understood that the pump 4005 can be used to infuse drugs within the body, by connecting the outlet port 4014, via a conduit, to the locale where the drug is to be dispensed. Alternatively, the drug infusion conduits can be connected to the output ports 4040, with the suction ports 4023 being closed (or not included).

The pump 4005 can be used to replace other internal organs which compress, expand or pump body fluids. It should be noted that when the pumps 4005 and 4007 are used as a heart replacement, they can dispense with the need for valves, or, in other words, the present artificial heart can replace the entire natural heart.

While particular embodiments of the present invention have been disclosed, it is to be understood that various different modifications are possible and are contemplated within the scope of the specification, drawings, abstract and appended claims.

What is claimed is:

1. A body organ replacement for replacing a body organ having at least one inlet fluid vessel and at least one outlet fluid vessel, the body organ replacement comprising:

a motor-driven scroll type pump including:
   a) a biocompatible housing sized to fit within a body cavity including at least one inlet port and one outlet port, said ports to be connected to a vascular system of the body;
   b) a first and a second scroll involute elements interfitting to make a plurality of line contacts therebetween, for defining at least one pair of fluid pockets; and c) at least said first element moving in an orbital motion relative to said second element, such that said line contacts shift and cause said at least one pair of fluid pockets to change in volume while shifting toward said at least one outlet port, with the volume of each fluid pocket being gradually changed.

2. The body organ replacement according to claim 1, wherein said second element is fixed and said first element moves relative to said second element.

3. The body organ replacement according to claim 1, wherein said housing is hermetically sealed and biocompatible for implantation.

4. The body organ replacement according to claim 1, wherein said inlet port includes a valve which will open at a predetermined pressure.

5. The body organ replacement according to claim 1, further including a plurality of suction ports which allow a second fluid to enter said pump and to mix with a first fluid passing through said inlet port and captured within said at least one pair of fluid pockets.

6. The body organ replacement according to claim 5, wherein the mixture of said first and second fluids exits through said outlet port as an outlet fluid; and wherein said outlet fluid is pulsated by selectively controlling the opening and closing of said inlet port and suction ports.

7. The body organ replacement according to claim 6, wherein said first fluid is blood; and wherein said second fluid is a drug to be infused into said first fluid.

8. The body organ replacement according to claim 6, wherein said first fluid is blood; and wherein said second fluid has a gaseous composition.

9. The body organ replacement of claim 8, wherein said second fluid is oxygen.

10. The body organ replacement of claim 1, wherein the volume of one of said fluid pockets is gradually reduced.

11. The body organ replacement of claim 1, wherein the volume of one of said fluid pockets is gradually increased.

12. The body organ replacement of claim 1, wherein both of said first and second elements move relative to each other.

13. The body organ replacement of claim 1, further including one or more outlets ports for regulating the pressure in said fluid pockets.

14. A heart replacement for replacing a natural heart, comprising:

at least one motor-driven scroll type pump including:
a) a biocompatible housing sized to fit within a body cavity including at least one inlet port and one outlet port, said ports to be connected to a vascular system of the body;

b) a first and a second scroll involute elements interfitting to make a plurality of line contacts therebetween, for defining at least one pair of fluid pockets; and c) at least said first element moving in an orbital motion relative to said second element, such that said line contacts shift and cause said at least one pair of fluid pockets to change in volume while shifting toward said at least one outlet port, with the volume of each fluid pocket being gradually changed.

15. A drug infusion pump comprising: at least one motor-driven scroll type pump including:
a) a biocompatible housing sized to fit within a body cavity including at least one inlet port and one outlet port, said ports t be connected to a vascular system of the body;

b) a first and a second scroll involute elements interfitting to make a plurality of line contacts therebetween, for defining at least one pair of fluid pockets; and c) at least said first element moving in an orbital motion relative to said second element, such that said line contacts shift and cause said at least one pair of fluid pockets to change in volume while shifting toward said at least one outlet port, with the volume of each fluid pocket being gradually changed.

16. The drug infusion pump of claim 15, wherein said second element is fixed and said first element moves relative to said second element.

17. The drug infusion pump of claim 15, wherein said housing is hermetically sealed and biocompatible for implantation.

18. The drug infusion pump of claim 15, wherein said inlet port includes a valve which opens at a predetermined pressure.

19. The drug infusion pump of claim 15, wherein the volume of one of said fluid pockets is gradually reduced; and further including one or more outlet ports for regulating the pressure in said fluid pockets.

20. The drug infusion pump of claim 19, further including a plurality of suction ports which allow a second fluid to enter said pump and to mix with a first fluid passing through said inlet port and captured within said at least one pair of fluid pockets;

wherein the mixture of said first and second fluids exits through said outlet port as an outlet fluid;

wherein said outlet fluid is pulsated by selectively controlling the opening and closing of said inlet port and suction ports; and wherein said first fluid is a drug to be infused.

* * * * *